United States Patent [19]

Takayama

[11] Patent Number: 4,535,771

[45] Date of Patent: Aug. 20, 1985

[54] CALCULUS DISINTEGRATING APPARATUS

[75] Inventor: Syuichi Takayama, Tokyo, Japan

[73] Assignee: Olympus Optical Co., Ltd., Tokyo, Japan

[21] Appl. No.: 449,699

[22] Filed: Dec. 14, 1982

[30] Foreign Application Priority Data

| | | | |
|---|---|---|---|
| Dec. 22, 1981 | [JP] | Japan | 56-206107 |
| Dec. 26, 1981 | [JP] | Japan | 56-214252 |
| Jan. 19, 1982 | [JP] | Japan | 57-6576 |

[51] Int. Cl.³ ........................ A61B 17/22; A61B 17/36

[52] U.S. Cl. ........................ 128/328

[58] Field of Search .............. 128/328, 303.14, 303.13, 128/422

[56] References Cited

U.S. PATENT DOCUMENTS

| | | | |
|---|---|---|---|
| 3,413,976 | 12/1968 | Roze | 128/328 |
| 3,563,247 | 2/1971 | Bowers | 128/422 |
| 3,735,764 | 5/1973 | Balev et al. | 128/328 |
| 3,785,382 | 1/1974 | Schmidt-Kloiber et al. | 128/328 |
| 3,902,499 | 9/1975 | Shene | 128/328 |
| 4,019,510 | 4/1977 | Ellis | 604/20 |
| 4,114,623 | 9/1978 | Meinke et al. | 128/303.14 |
| 4,191,189 | 3/1980 | Barkan | 128/328 |
| 4,271,837 | 6/1981 | Schuler | 128/303.14 |
| 4,301,801 | 11/1981 | Schneiderman | 128/303.14 |
| 4,340,047 | 7/1982 | Tapper et al. | 604/20 |

FOREIGN PATENT DOCUMENTS

| | | | |
|---|---|---|---|
| 707011 | 3/1965 | Canada | 128/419 R |

*Primary Examiner*—Michael H. Thaler

*Attorney, Agent, or Firm*—Frishauf, Holtz, Goodman & Woodward

[57] ABSTRACT

A calculus disintegrating apparatus includes first and second electrodes which are arranged at the distal end of a probe inserted into a coeliac cavity, and discharge energy sources connected to the first and second electrodes to impresses D.C. impulse voltage across them. The apparatus is arranged to crush a calculus by impact wave resulting from spark discharges produced across the first and second electrodes. A polarity changing circuit is provided between the discharge energy sources and first and second electrodes to vary the polarity of the output D.C. impulse voltage from the discharge energy sources.

4 Claims, 20 Drawing Figures

CALCULUS DISINTEGRATING APPARATUS

BACKGROUND OF THE INVENTION

This invention relates to a calculus disintegrating apparatus. A calculus disintegrating apparatus has been developed which produces spark discharges in a coeliac liquid surrounding a calculus, to disintegrate the calculus by the resultant hydraulic impact wave. Such a calculus disintegrating apparatus generally comprises two electrodes set at the distal end of a probe inserted into a coeliac cavity and a power supply section which impresses D.C. impulse voltage on the electrodes to generate spark discharges across the electrodes. The power supply section is provided with a capacitor, and causes the discharge current to flow across the electrodes for production of spark discharges. The electrodes are generally prepared from tungsten alloy. Each electrode is slowly consumed with time due to the impression of discharge energy. During the use of the electrodes, the end of the anode, in particular is rounded, resulting in a rise in the voltage requuired for the initiation of spark discharges. When a spark discharge initiating voltage rises beyond the voltage with which the capacitor is charged, then spark discharges fail to be produced. This means that consumption of an electrode shortens the effective life thereof. Moreover, it is impossible to recognize the extent of the depletion of the electrode by the naked eye, thus failing to define an optimum point of time at which the used electrode is to be exchanged for a fresh one. While a patient is undergoing a treatment, it sometimes happens that the effective life of an electrode comes to an end. Such an event increases the time of treatment and the pain suffered by a patient.

SUMMARY OF THE INVENTION

It is accordingly an object of this invention to extend the effective life of a calculus disintegrating apparatus which crushes a calculus by hydraulic impact waves resulting from spark discharges.

To attain the above-mentioned object, this invention provides a calculus disintegrating apparatus which comprises first and second electrodes provided separately from each other, a capacitor connected between the first and second electrodes, a power source for charging the capacitor, a circuit allowing for the passage of a discharge current across the first and second electrodes, and switching circuit for changing the direction in which the discharge current flows.

DETAILED DESCRIPTION OF THE PREFERRED EMBODIMENTS

Figure 1:
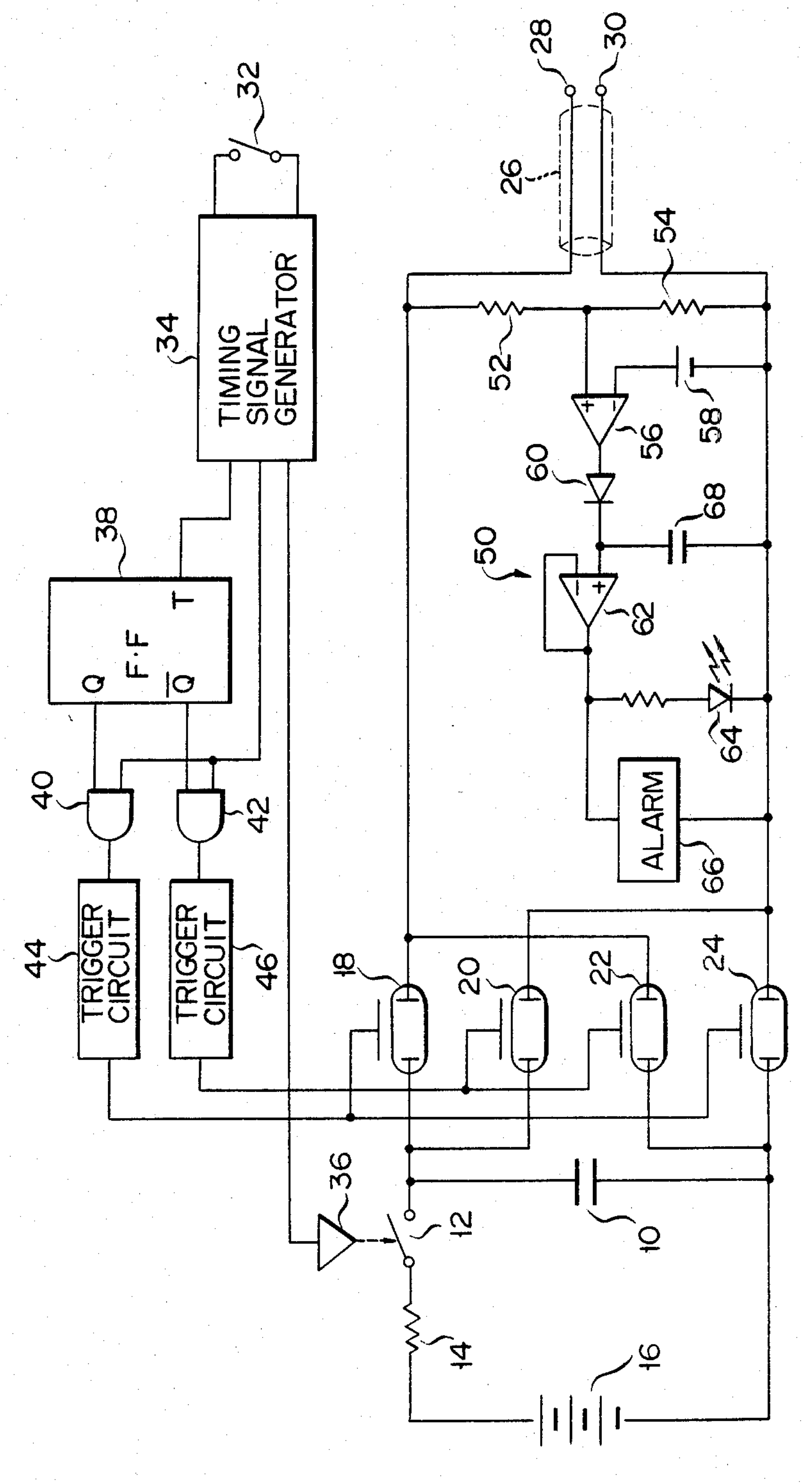
FIG. 1 is a block circuit diagram of a calculus disintegrating apparatus according to a first embodiment of this invention.

FIG. 1 is a block diagram of the first embodiment. A capacitor 10 is connected to a D.C. power source 16 through a series-connected switch 12 and resistor 14. One end of the capacitor 10 is connected to discharge tubes 18 and 20 each at one end. The other end of the capacitor 10 is connected to discharge tubes 22 and 24 each at one end. The other ends of the discharge tubes 18 and 22 are connected together, and also to an electrode 28 through a probe 26. The other ends of the discharge tubes 20 and 24 are connected together, and also to an electrode 30 through the probe 26. The probe 26 is inserted into a coeliac cavity through, for example, a forceps channel of an endoscope. The electrodes 28 and 30 are so closely spaced from each other that spark discharge are easily produced across the electrodes 28 and 30 by a discharge current supplied from the capacitor 10. When the discharge tubes 18 and 24 are rendered conductive, current flows across the electrodes 28 and 30 in a direction different from when the discharge tubes 20 and 22 are rendered conductive. In other words, the discharge tubes 18, 20, 22 and 24 jointly constitute a polarity-changing circuit to alter the direction in which spark discharges are produced.

A first output terminal of a timing signal generator 34 having a trigger switch 32 is connected to an actuator 36. When supplied with a signal having a logic level "1", the actuator 36 closes the switch 12. A third output terminal of the timing signal generator 34 is connected to an input terminal of a T flip-flop circuit 38, and a second output terminal of the timing signal generator 34 is connected to first input terminals of AND gates 40 and 42. The output terminals Q and $\overline{Q}$ of the flip-flop circuit 38 are respectively connected to second input terminals of the AND gates 40 and 42. The output terminals of the AND gates 40 and 42 are respectively connected to trigger circuits 44 and 46. An output signal from the trigger circuit 44 is supplied to trigger electrodes of the discharge tubes 18 and 24. An output signal from the trigger circuit 46 is supplied to trigger electrodes of the discharge tubes 20 and 22.

A warning circuit 50 is connected between the electrodes 28 and 30 for detecting the level of voltage impressed across the terminals of the electrodes 28 and 30, and, when the discharge initiating voltage rises beyond a prescribed level, lights an alarm lamp and also gives a sound alarm. The warning circuit 50 is arranged as described below. Resistors 52 and 54 are connected in series between the electrodes 28 and 30. The junction of the resistors 52 and 54 is connected to a noninverting input terminal of a comparator 56. A D.C. source 58 is connected to an inverting input terminal of the comparator 56. An output signal from the comparator 56 is supplied to a light-emitting diode (LED) 64 and alarm circuit 66 through a diode 60 and buffer 62. The input terminal of the buffer 62 is connected to a capacitor 68.

Figure 2A:
FIGS. 2A to 2E are timing charts showing the operation of the calculus disintegrating apparatus of FIG. 1.
Figure 2B:
Figure 2C:

Description will now be given with reference to the timing charts of FIGS. 2A to 2E, of the operation of a calculus disintegrating apparatus according to the first embodiment of this invention. When power is supplied to the timing signal generator 34, a pulse having a logic level "1" is issued from the first output terminal of the timing signal generator 34 to the actuator 36 (FIG. 2A). As a result, the switch 12 is closed to cause the capacitor 10 to be charged by the D.C. source 16 (FIG. 2B). The period of time during which the switch 12 remains closed, that is, the pulse width of the first output signal is defined by the capacitance of the capacitor 10 and the resistance of the resistor 14. The capacitor 10 is charged to the same potential as the D.C. source 16. Thus the subject calculus disintegrating apparatus is brought to a standby state.

Figure 2D:
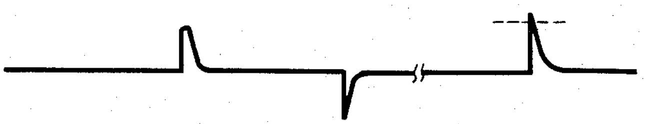
Figure 2E:
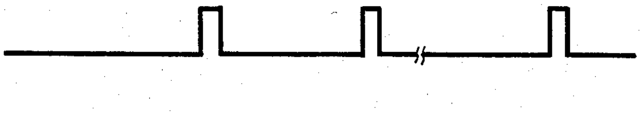

Now let it be assumed that the flip-flop circuit 38 is set. The electrodes 28 and 30 are drawn near the calculus of a patient, and the trigger switch 32 is closed. At this time, the timing signal generator 34 sends forth a pulse signal having a logic level "1" (FIG. 2C) from the second output terminal. The AND gate 40 and consequently the trigger circuit 44 are rendered conductive. The discharge tubes 18 and 24 are rendered conductive, causing an output discharge current from the capacitor 10 to flow through the discharge tube 24, electrodes 30 and 28 and discharge tube 18. As a result, a D.C. inpulse voltage is impressed across the electrodes 28 and 30 (FIG. 2D). A discharge current flows from the electrode 30 to the electrode 28. An impact wave is produced to disintegrate a calculus. The timing signal generator 34 sends forth a pulse signal having a logic level "1" (FIG. 2E) from a third output terminal in a prescribed length of time after the issue of a second output signal. As a result, the flip-flop circuit 18 is reset. The first output pulse is automatically sent forth at a prescribed length of time after the issue of the third output signal. When the trigger switch 32 is again closed, the AND gate 42 and consequently the trigger circuit 46 are rendered conductive. Since the discharge tubes 20 and 22 are rendered conductive, an output discharge current from the capacitor 10 flows through the discharge tube 22, electrodes 28 and 30, and discharge tube 20. In other words, the discharge current flows in the opposite direction to the aforementioned case.

With the above-mentioned calculus disintegrating apparatus according to the first embodiment, a discharge current flows in the opposite direction for each discharge, preventing only one anode electrode from being established, and enabling the anode electrode to be consumed at half the rate which is observed in the conventional calculus disintegrating apparatus. Therefore, electrode life can be substantially doubled.

When discharge is carried out very frequently, then the electrodes 28 and 30 are noticeably consumed, leading to a rise in the discharge initiating voltage and presenting difficulties in producing spark discharges. When, with the first embodiment, the voltage across the electrodes 28 and 30 rises above the D.C. voltage 58 indicated by a broken line in FIG. 2D, then the LED 64 emits light and the alarm circuit 66 gives an alarm, thereby notifying the operator of the time at which the electrodes 28 and 30 are to be exchanged for fresh ones.

Figure 3:
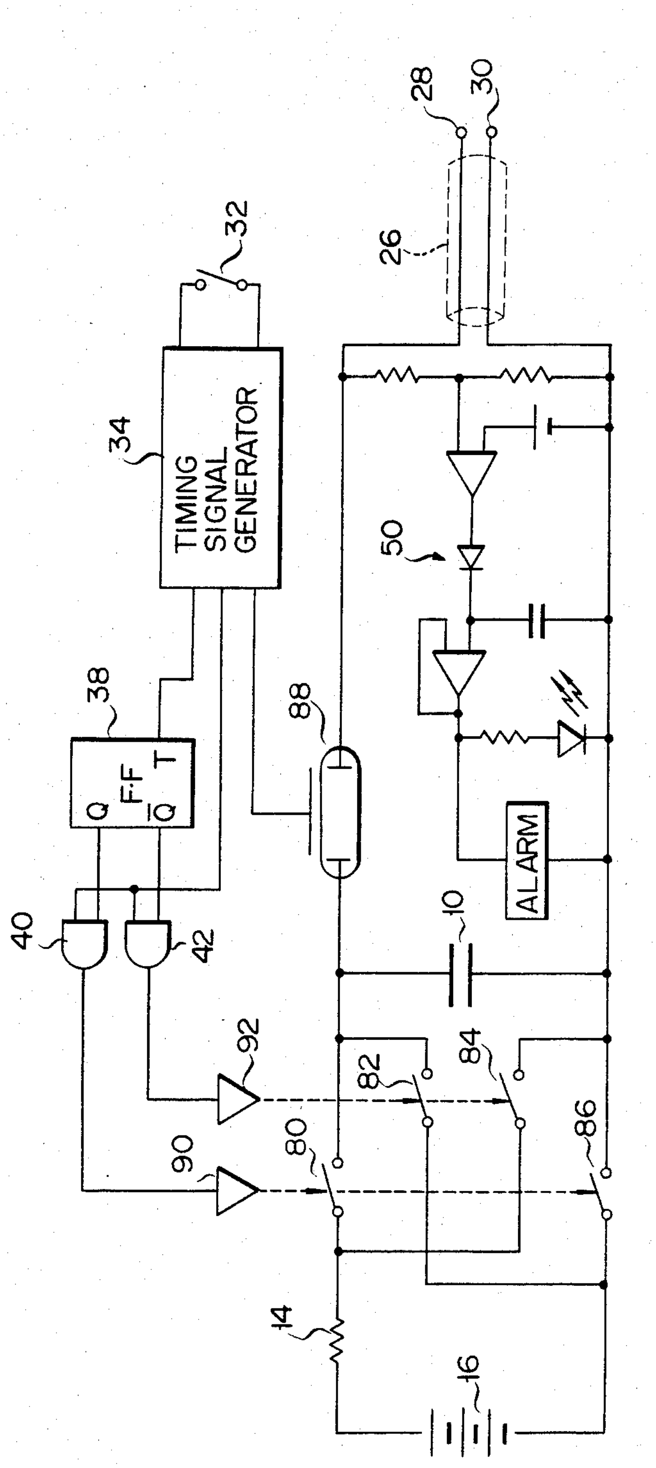
FIG. 3 is a block circuit diagram of a calculus disintegrating apparatus according to a second embodiment of the invention.

Description will not be given of other embodiments of a calculus disintegrating apparatus of this invention. The reference numerals used in the first embodiment will be used for corresponding elements in the other embodiments. A second embodiment shown in FIG. 3 is different from the first embodiment in that the second embodiment comprises a single discharge circuit, not two discharge circuits. One terminal of a capacitor 10 is selectively to positive and negative terminals of a D.C. source 16 through switches 80 and 82. The other end of the capacitor 10 is selectively to the positive and negative terminals of the D.C. source 16 through switches 84 and 86. A discharge tube 88 is connected to the discharge circuit of the capacitor 10. A first output terminal of a timing signal generator 34 is connected to first input terminals of AND gates 40 and 42. A second output terminal of the timing signal generator 34 is connected to a trigger terminal of the discharge tube 88. A third output terminal of the timing signal generator 34 is connected to an input terminal of a flip-flop circuit 38 as in the first embodiment. Output signals from the AND gates 40 and 42 are respectively supplied to actuators 90 and 92.

Figure 4A:
FIGS. 4A to 4E are timing charts showing the operation of the second embodiment.
Figure 4B:
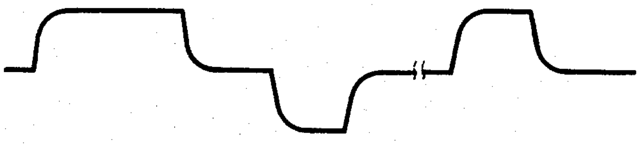
Figure 4C:
Figure 4D:
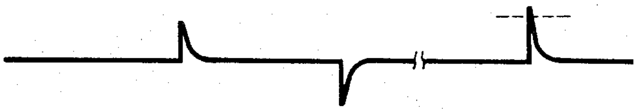
Figure 4E:
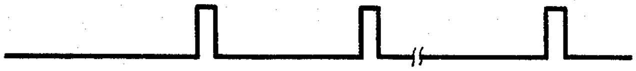

Description will now be given with reference to the timing charts of FIGS. 4A to 4E of the operation of the calculus disintegrating apparatus according to the second embodiment. FIGS. 4A to 4E respectively correspond to FIGS. 2A to 2E. A first output signal (FIG. 4A) from the timing signal generator 34 is supplied to the AND gates 40 and 42. Now let it be assumed that the flip-flop circuit 38 is set. Then, the AND gate 40 is rendered conductive, causing the switches 80 and 86 to be closed. The capacitor 10 is charged as shown in FIG. 4B. Later when the trigger switch 32 is closed, causing the timing signal generator 34 to issue a pulse signal (FIG. 4C) from the second output terminal, then the discharge tube 88 is rendered conductive, and an output discharge current from the capacitor 10 flows through the electrodes 30 and 28 and discharge tube 88. A pulse signal (FIG. 4E) is issued from the third output terminal of the timing signal generator 34, causing the flip-flop circuit 38 to be reset. Later when the timing signal generator 34 sends forth a first output signal (FIG. 4A), the AND gate 42 is rendered conductive, causing the switches 82 and 84 to be closed. The capacitor 10 is charged with the opposite polarity to the aforementioned case as indicated in FIG. 4B. When the discharge tube 88 is rendered conductive, a discharge current flows in the opposite direction to the above-mentioned case, causing voltage to be impressed across the electrodes 28 and 30 with the opposite polarity shown in FIG. 4D.

Even when the direction in which charge current is supplied to the capacitor 10 is changed as described above, the two electrodes 28 and 30 are alternately used as an anode as in the first embodiment. Therefore, the second embodiment has the same effect as the first embodiment. The warning circuit 50 has the same function as in the aforementioned case, description thereof being omitted.

With the above two embodiments, the direction in which the discharge current flows is altered each time by altering the discharge circuit or charge circuit. However, this alternative need not be performed each time. It is possible to alter the direction of the discharge current for every several discharges. Further, it is possible to alter the discharge direction after one electrode is so consumed as to fail to produce a spark discharge.

Figure 5:
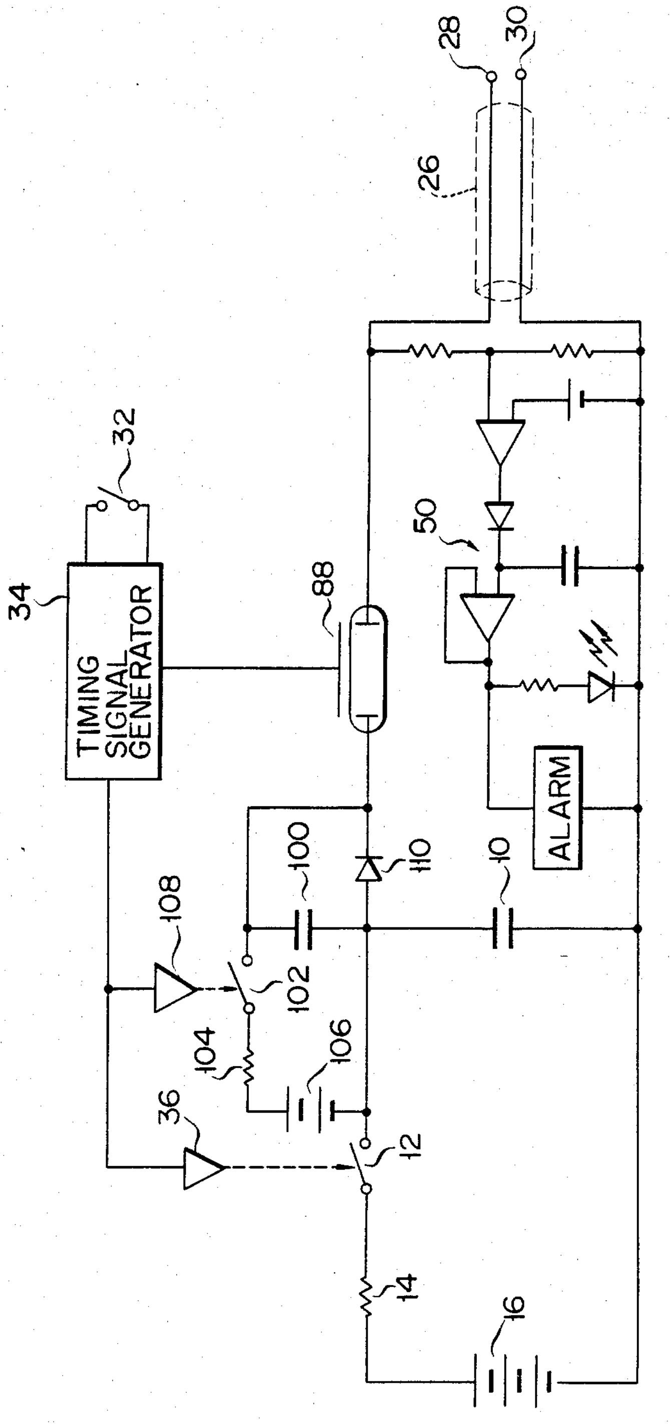
FIG. 5 is a block diagram of a calculus disintegrating apparatus according to a third embodiment of the invention.

FIG. 5 is a block diagram of a calculus disintegrating apparatus according to a third embodiment of this invention. The third embodiment comprises a single switch 12 for charging a capacitor 10 and a single discharge tube 88. An auxiliary capacitor 100 is connected in series to the capacitor 10. Discharge currents from both capacitors 100 and 10 are conducted to electrodes 28 and 30 through the discharge tube 88. The auxiliary capacitor 100 is connected to an auxiliary power source 106 through a switch 102 and a resistor 104. The auxiliary capacitor 100 has a smaller capacitance than the capacitor 10. A timing signal generator 34 has first and second output terminals. The first output terminal is connected to actuators 36 and 108, and the second output terminal is connected to a trigger terminal of the discharge tube 88. The actuators 36 and 108 are respectively operated to close switches 12 and 102. The junction of the capacitors 10 and 100 is connected to the discharge tube 88 through a diode 110. A warning circuit 50 is connected between the electrodes 28 and 30.

Figure 6A:
FIGS. 6A to 6D are timing charts indicating the operation of the third embodiment.
Figure 6B:
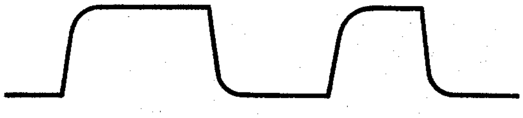
Figure 6C:
Figure 6D:
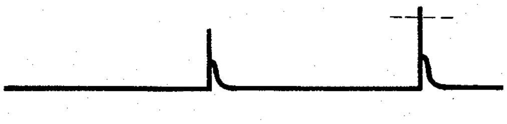

When, with the third embodiment of FIG. 5, the timing signal generator 34 issues a pulse signal (FIG. 6A) from the first output terminal, then the actuators 36 and 108 are operated to close the switches 12 and 102. Power from the D.C. sources 16 and 106 is supplied to the series-connected capacitors 10 and 100 (FIG. 6B). When the trigger switch 32 is closed, and the timing signal generator 34 issues a pulse signal (FIG. 6C) from the second output terminal, then the discharge tube 88 is rendered conductive, causing the capacitors 10 and 100 to be discharged. In this case, the auxiliary capacitor 100 has a smaller capacitance than the capacitor 10, and is instantly discharged. At the initiation of discharge, a sum of the voltages impressed on the capacitors 10 and 100 is supplied across the electrodes 28 and 30 (FIG. 6D). Soon, a voltage discharged from the capacitor 10 alone is applied across the electrodes 28 and 30, thereby facilitating the occurrence of spark discharges across the electrodes 28 and 30. Therefore, countermeasures can be taken for even the rise in the discharge initiating voltage which is caused by the depletion of an electrode. High voltage is only required at the initiation of discharge. Therefore, the reason why the auxiliary capacitor 100 is chosen to have a smaller capacitance than the capacitor 10 is that this process enables D.C. power 106 to be effectively supplied. When the discharge initiating voltage rises above a prescribed level as shown in FIG. 6D, the warning circuit 50 is actuated to inform the operator to exchange the electrode.

As described above, the third embodiment comprises not only the ordinary capacitor 10, but also the auxiliary capacitor 100. Since the voltage of the auxiliary capacitor 100 is impressed across the electrodes 28 and 30 in addition to the voltage of the capacitor 10, spark discharges can be easily produced, enabling an electrode life to be extended more than in the conventional calculus disintegrating apparatus.

Figure 7:
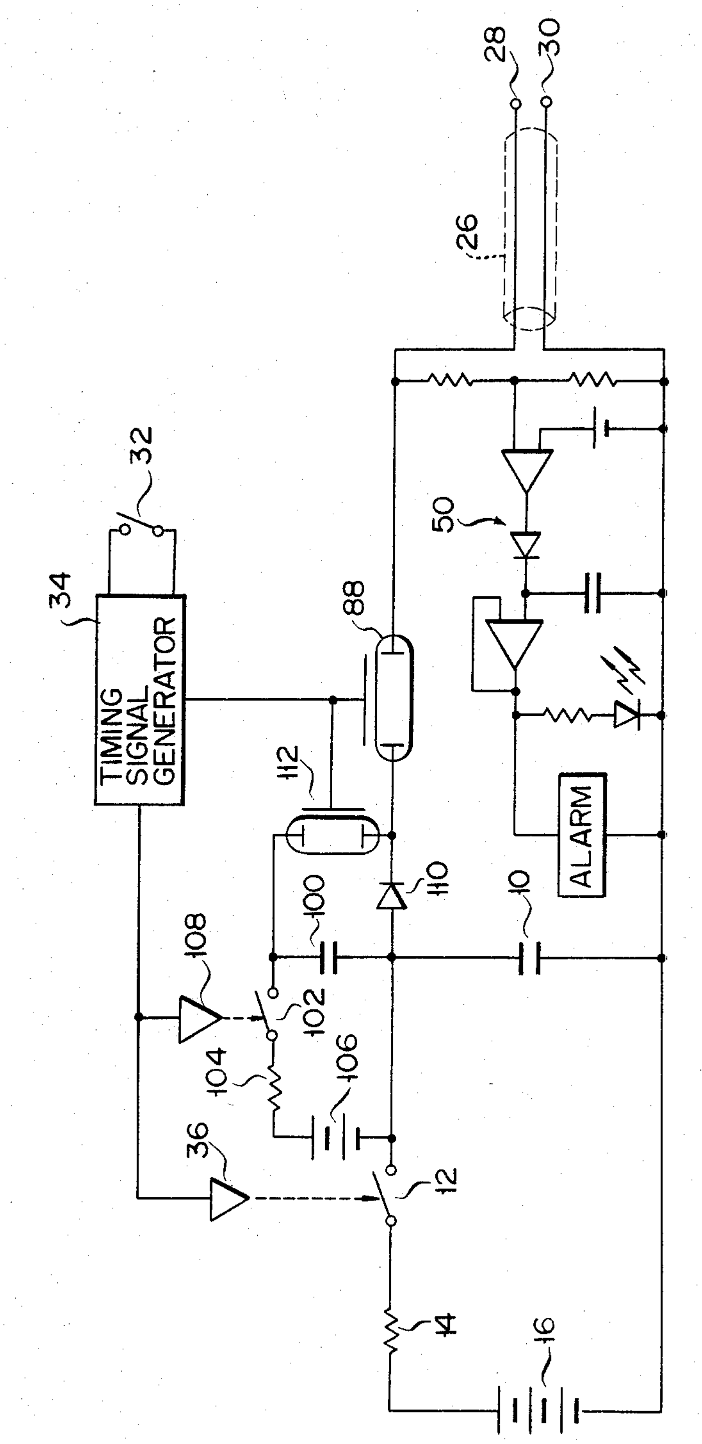
FIG. 7 is a block diagram of a modification of the third embodiment.

Description will now be given with reference to FIG. 7 of a modification of a calculus disintegrating apparatus of the third embodiment. With the third embodiment, a discharge tube 112 is provided in the discharge circuit of the capacitor 100, and the second output terminal of the timing signal generator 34 is connected to the trigger terminals of the discharge tubes 88 and 112. The discharge circuit for the capacitor 100 is formed only when the trigger switch 32 is closed, and the discharge tube 112 is rendered conductive. Therefore, the natural discharge of the capacitor 100 is suppressed.

Figure 8:
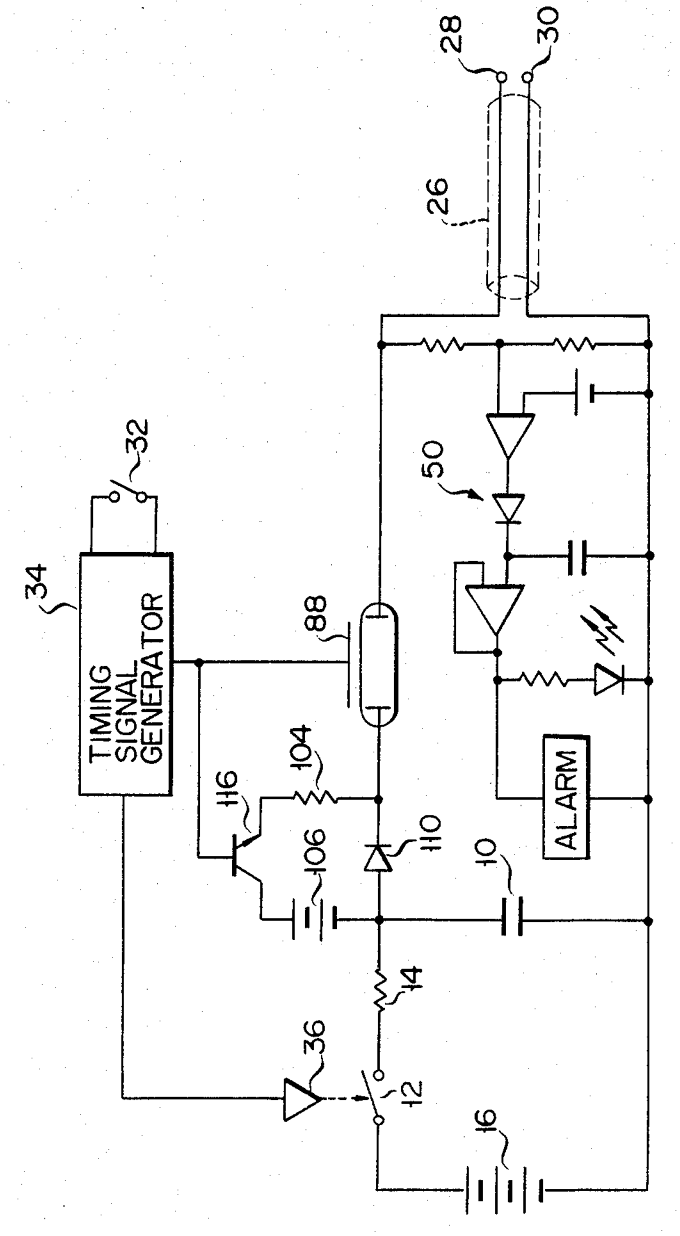
FIG. 8 is a block diagram of a calculus disintegrating apparatus according to a fourth embodiment of the invention.

Description is now given with reference to FIG. 8 of a fourth embodiment of this invention. The fourth embodiment is free from the capacitor 100 used in the third embodiment, and further the switch 102 of the third embodiment is replaced by a semiconductor switching element (NPN transistor) 116. The second output terminal of the timing signal generator 34 is connected to the base of the transistor 116 and the trigger terminal of the discharge tube 88. With the fourth embodiment, the timing signal generator 34 issues a second output pulse when the trigger switch 32 is closed, causing the transistor 116 and discharge tube 88 to be rendered conductive. The discharge tube 88 remains conductive until the discharge of the capacitor 10 is brought to an end, while the transistor 116 is rendered conductive only during the period of the second output pulse from the timing signal generator 34. At the initiation of discharge, therefore, a sum of the voltage of the capacitor 10 and that of the D.C. source 106 is impressed across the electrodes 28 and 30, thereby allowing for easy spark discharge.

With the third and fourth embodiments, higher voltage is impressed across the electrodes 28 and 30 at the initiation of discharge than in the conventional calculus disintegrating apparatus, thereby assuring the production of discharge even when the electrodes are appreciably depleted and substantially extending electrode life. High voltage is impressed only at the initiation of discharge, thereby saving excess power consumption.

Figure 9:
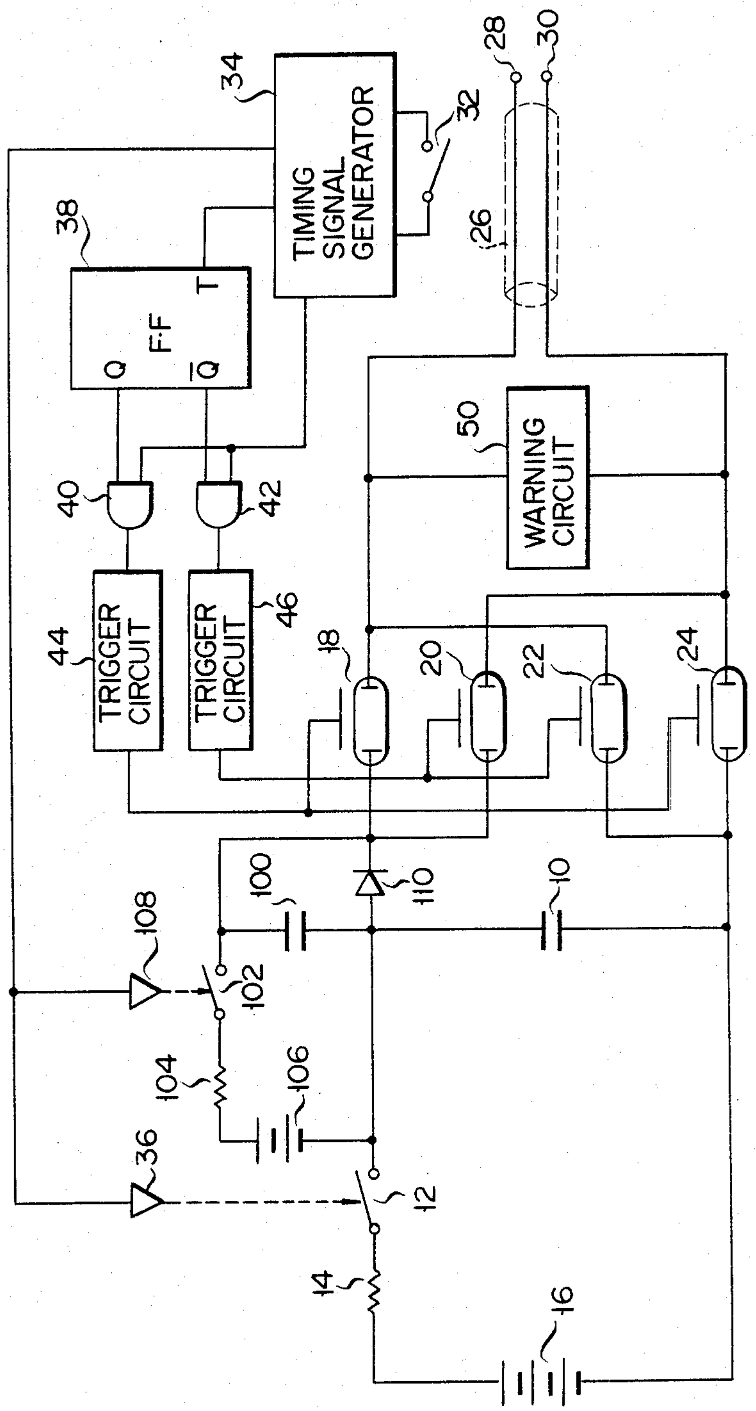
FIG. 9 is a block diagram of a fifth embodiment achieved by assembling of the first and third embodiments.

This invention is not limited to the aforementioned embodiments, but is applicable with various modifications and changes. It is possible to assemble either of the first and second embodiments with either of the third and fourth embodiments. FIG. 9 shows a block diagram of a fifth embodiment of the invention by assembling the first embodiment of FIG. 1 with the third embodiment of FIG. 5. With the third and fourth embodiments, high voltage is always applied at the initiation of discharge. However, it is possible to detect how much the electrodes are depleted when discharge is going to be started, and, if the depletion appreciably advances, to impress high voltage on the electrodes. The warning circuit 50 may detect a voltage impressed across the discharge tube 88 as a discharge initiating voltage. When the electrodes are depleted, the voltage of the capacitor 10 is raised when discharge is brought to an end. Therefore, it is possible to detect the voltage of the capacitor 10 at the termination of discharge and issue a warning signal according to the level of voltage detected.

What is claimed is:

1. A calculus disintegrating apparatus, which comprises:

first and second electrodes provided separately from each other;

discharge energy source means including a D.C. power source and a capacitor arranged to be charged by the D.C. power source, wherein said discharge energy source means is connected to said first and second electrodes to apply a D.C. impulse voltage across said first and second electrodes when the capacitor is discharged;

polarity changing means which is connected to said capacitor, and arranged to change the polarity of D.C. impulse voltage applied across said first and second electrodes in response to each discharge of said capatitor;

wherein said polarity changing means comprises a switching circuit connected between said capacitor and said D.C. power source for selectively defining the direction in which charge current flows from said D.C. power source to said capacitor; and said switching circuit comprises a first switch connected between one end of said capacitor and the positive terminal of said D.C. power source, a second switch connected between said one end of said capacitor and the negative terminal of said D.C. power source, a third switch connected between the other end of said capacitor and the positive terminal of said D.C. power source, a fourth switch connected between the other end of said capacitor and the negative terminal of said D.C. power source, a first actuator for closing said first and said fourth switches, a second actuator for closing said second and said third switches, and a flip-flop circuit having a trigger input connected to receive switch signals for alternately operating said first and said second actuators in response to each succeeding switch signal applied to said trigger input.

2. A calculus disintegrating apparatus according to claim 1, in which said polarity changing means comprises a switching circuit which is connected between the capacitor and the first and second electrodes, and selectively defines the direction in which discharge current flows from the capacitor to the first and second electrodes.

3. A calculus disintegrating apparatus according to claim 1, which further comprises a warning circuit which detects discharge initiating voltage applied across the first and second electrodes, and, when the detected voltage is higher than a prescribed level, gives an alarm.

4. A calculus disintegrating apparatus according to claim 3, in which said switching circuit comprises a first discharge tube connected between one end of the capacitor and said first electrode, a second discharge tube connected between said one end of the capacitor and said second electrode, a third discharge of the capacitor tube connected between the other end of the capacitor and said first electrode, a fourth discharge tube connected between the other end of the capacitor and said second electrode, a first trigger circuit for triggering said first and fourth discharge tubes, a second trigger circuit for triggering said second and third discharge tubes, and a flip-flop circuit for alternately selecting said first and second trigger circuits each time the initiation of discharge is instructed.

* * * * *